(12) United States Patent
Dalibor

(10) Patent No.: US 8,731,852 B2
(45) Date of Patent: May 20, 2014

(54) METHOD FOR ANALYSING PHOTOVOLTAIC LAYER SYSTEMS USING THERMOGRAPHY

(75) Inventor: Thomas Dalibor, Herrsching am Ammersee (DE)

(73) Assignee: Saint-Gobain Glass France, Courbevoie (FR)

( * ) Notice: Subject to any disclaimer, the term of this patent is extended or adjusted under 35 U.S.C. 154(b) by 0 days.

(21) Appl. No.: 13/819,845

(22) PCT Filed: Sep. 28, 2011

(86) PCT No.: PCT/EP2011/066898
§ 371 (c)(1),
(2), (4) Date: May 16, 2013

(87) PCT Pub. No.: WO2012/052269
PCT Pub. Date: Apr. 26, 2012

(65) Prior Publication Data
US 2013/0226480 A1    Aug. 29, 2013

(30) Foreign Application Priority Data

Sep. 28, 2010   (EP) .................................... 10180708

(51) Int. Cl.
*G01R 31/00* (2006.01)
*G01N 25/72* (2006.01)

(52) U.S. Cl.
USPC ............. 702/58; 382/145; 382/146; 382/147; 382/149

(58) Field of Classification Search
USPC .............. 702/57–59, 179–183, 185; 324/537; 382/145–147, 149
See application file for complete search history.

(56) References Cited

U.S. PATENT DOCUMENTS

| | | | |
|---|---|---|---|
| 6,813,032 B1 * | 11/2004 | Hunter | 356/601 |
| 7,471,817 B2 * | 12/2008 | Olschewski et al. | 382/133 |
| 8,071,875 B2 * | 12/2011 | Li | 136/264 |
| 8,417,011 B2 * | 4/2013 | Klottrup et al. | 382/133 |
| 2004/0081618 A1 * | 4/2004 | Enoki et al. | 424/9.1 |
| 2010/0074515 A1 * | 3/2010 | Zhao et al. | 382/149 |
| 2010/0182421 A1 | 7/2010 | Chidambaram et al. | |
| 2010/0201374 A1 * | 8/2010 | Vasilyev et al. | 324/538 |

FOREIGN PATENT DOCUMENTS

WO     2011/016420     10/2011

OTHER PUBLICATIONS

PCT International Search Report mailed on Feb. 2, 2012 for PCT Application PCT/2011/066898 filed on Sep. 28, 2011 in the name of Saint-Gobain Glass France (English + German).

(Continued)

*Primary Examiner* — Michael Nghiem
*Assistant Examiner* — Alexander Satanovsky
(74) *Attorney, Agent, or Firm* — Steinfl & Bruno LLP

(57) ABSTRACT

A method for the evaluative analysis of a photovoltaic layer system is described. The method applies to a semiconductor layer forming a pn junction: an electric current is generated in the layer system; a spatially resolved thermal image of the surface of the layer system is generated; an intensity distribution of the thermal radiation relative to the respective number of pixels with the same intensity value is determined; an intensity mean/median from the intensity distribution is determined; an intensity interval based on a specifiable measure for a scattering of the intensity distribution is determined; a characteristic number is determined; and the characteristic number or a calculation value based thereon is compared with a specifiable reference characteristic number.

16 Claims, 3 Drawing Sheets

(56) References Cited

OTHER PUBLICATIONS

PCT International Preliminary Report on Patentability issued on Apr. 2, 2013 for PCT Application No. PCT/EP2011/066898 filed on Sep. 28, 2011 in the name of Saint-Gobain Glass France et al. (German + English).

Breitenstein et al., Quantitative evaluation of shunts in solar cells by lock-in thermography, Prog. In Photovoltaics: Research & Applications 2003, 11: 515-526.

* cited by examiner

METHOD FOR ANALYSING PHOTOVOLTAIC LAYER SYSTEMS USING THERMOGRAPHY

CROSS REFERENCE TO RELATED APPLICATIONS

The present application is the U.S. national stage of International Application PCT/EP2011/066898 filed on Sep. 28, 2011 which, in turn, claims priority to European Patent Application EP 10180708.9 filed on Sep. 28, 2010.

BACKGROUND

The invention is in the technical area of the production of devices for photovoltaic energy generation and relates to a method for the evaluative, quantitative analysis of photovoltaic layer systems.

Solar cells enable direct conversion of light radiation into electrical current. With respect to efficiency, thin-film solar cells based on polycrystalline chalcopyrite semiconductors have proved to be advantageous. In particular, copper indium diselenide ($CuInSe_2$ or CIS) is distinguished by a particularly high absorption coefficient because of its band gap suited to the spectrum of sunlight. For adequate mechanical strength, thin-film solar cells require special carrier substrates, which, for the most part, contain inorganic glass, polymers, or metal alloys, and can, depending on the layer thickness and material properties, be implemented as rigid plates or flexible films. Since, typically, with individual solar cells, only voltage levels of less than 1 volt can be obtained, many solar cells are usually serially connected in a solar module in order to thus obtain a technically useful output voltage. For this, thin-film solar modules offer the particular advantage that the solar cells can already be connected serially in an integrated form during production of the films. To ensure lasting protection against environmental influences, the solar cells are customarily combined with low-iron soda lime glasses and adhesion-promoting polymer films into a weather-resistant composite.

However, during the production of solar modules, various kinds of defects can occur, which disadvantageously cause internal electrical power losses and thus reduce the efficiency of solar modules. Significant causes of such power losses are, for example, short circuits (shunts), which result in a locally elevated recombination rate of charge carriers, and relatively high series resistances, which result substantially from the ohmic resistances of metal contacts, feed lines, and semiconductor material as well as contact resistances of metal-to-semiconductor contacts. Moreover, mechanical defects, such as cracks, fractures, and delaminations or variations of material quality, can, for example, result in power losses.

In the series production of solar modules, it is important, in the context of satisfactory quality control, in particular to meet specific quality standards, to be able to identify solar modules with high internal power losses. It is known, for this purpose, to use special infrared measurement techniques in which an electric current is generated in the solar module and a thermal image of the surface of solar module is captured by an infrared camera. Since all basic processes in the solar cells are always associated with heat dissipation, and defects, such as short circuits and series resistances, are typically come along with relatively high power losses, these can be detected by a locally elevated temperature of the surface of the solar module. In the thermal image, the defects appear, for example, as brighter (warmer) spots ("hot spots") or regions. In the scientific literature, this procedure has already been thoroughly described in many publications. Merely by way of example, reference is made to the technical article entitled "Quantitative Evaluation of Shunts in Solar Cells by Lock-in Thermography" by O. Breitenstein et al. in "Progress in Photovoltaics: Research and Applications" (Prog. Photovolt: Res. Appl. 2003; 11:515-526) and the citations mentioned therein. Additional technical background can be found in the patent applications U.S. 2010/201374 A1 and U.S. 2010/182421 A1.

In the series production of solar modules, the thermal images are usually assessed visually, with a qualitative statement made concerning their quality based substantially on the experience of the inspector.

SUMMARY

In contrast, the object of the present invention consists in providing a quantitative analysis of solar modules which enables an automated evaluation of the quality of solar modules. This and other objects are accomplished according to the proposal of the invention by a method with the characteristics of the independent claim. Advantageous embodiments of the invention are indicated by the characteristics of the dependent claims.

DETAILED DESCRIPTION

Figure 1:
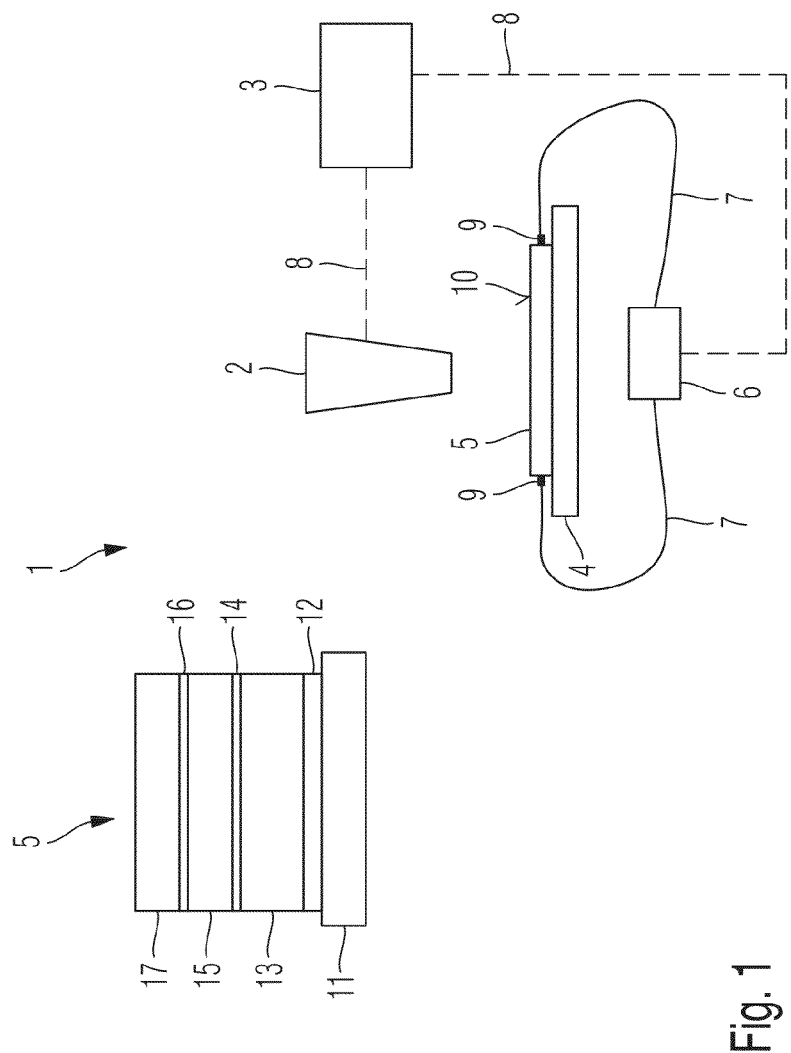
FIG. 1 shows a schematic representation of an exemplary setup for performance of the method according to the disclosure.

According to the invention, a method for the evaluative, quantitative analysis of a layer system for photovoltaic energy generation is demonstrated. In the layer system, a separation of the charge carriers or excitons takes place, for example, by internal electrical fields. The layer system preferably includes at least one semiconductor layer forming a heterojunction or pn junction, in other words, a sequence of regions with a different conductor type.

The photovoltaic layer system can, for example, be a (single) solar cell, several solar cells connected in series or as an array, or a solar module containing a large number of serially connected solar cells. In particular, the solar module can be a thin-film solar module, in which the solar cells are, for example, serially connected in an integrated form. Such a thin-film solar module typically includes at least one carrier substrate as well as a first electrode layer, a second electrode layer, and at least one semiconductor layer disposed between the two electrode layers. The semiconductor layer is customarily doped with a dopant. Alternatively, the semiconductor layer can be doped with a substance, for example, sodium, which results in intrinsic doping due to formation of native defects. Preferably, the semiconductor layer is made of a chalcopyrite compound, which can, in particular, be a I-III-VI-semiconductor from the group copper indium/gallium disulfide/diselenide ($Cu(In,Ga)(S,Se)_2$), for example, copper indium diselenide ($CuInSe_2$ or CIS), sodium-doped $Cu(In,Ga)(S,Se)_2$, or related compounds.

However, the photovoltaic layer system can also be an intermediate product in the production of solar cells or solar modules that includes at least one semiconductor layer forming a pn junction.

In the method according to the invention for the evaluative, quantitative analysis of the photovoltaic layer system, an electric current is generated in the layer system, by means of which, among other things, an electric power loss is effected in the region of defects of the layer system such that the defects are detectable by means of an elevated temperature of the surface of the layer system compared to the surrounding temperature. The electric current can be generated by applying an electric voltage to the layer system in the reverse- and/or forward-biased direction of the pn junction. However, it is also conceivable to generate the current in the layer system, without contact, by irradiation with light, wherein in this manner, in particular, intermediate products of the production of solar modules which do not yet have external electric connectors can be subjected, in a simple manner, to an evaluative, quantitative analysis by the method according to the invention.

In a temporal relation, in particular simultaneous with or nearly simultaneous with the generation of current, suitable for detecting the power loss generated by the current flow, a spatially resolved thermal image of the thermal radiation of the surface of the photovoltaic layer system is generated by means of a thermal imaging camera or an infrared camera. In solar modules, this can, in particular, be the surface provided for the incidence of light. Typically, the thermal image capturing the thermal radiation is based on a heat distribution of the surface of the layer system. Advantageously, the so-called "lock-in technique" is used, wherein a modulation method is used for the generation of current in the layer system. Since this procedure is not essential to the understanding of the invention and is well known to the person skilled in the art, it is superfluous to discuss it in further detail.

The (digital) thermal image is composed, as a digital raster image, of a large number of image points or image cells (pixels). Similarly, the surface of the layer system can, at least theoretically, be divided into a large number of surface elements each of which is biuniquely assigned one pixel of the thermal image. On the other hand, an intensity value corresponding to the surface temperature of the associated surface element is assigned to each pixel as a pixel value. In the thermal image, pixels, which correspond to points of the surface with a different surface temperature, have a different intensity value from one another. Pixels that correspond to warmer points of the surface appear brighter and, consequently, have a higher intensity value; whereas pixels that correspond to colder points appear darker and, consequently, have a lower intensity value. In an alternative scaling, a warmer point can correspond to a darker pixel and a colder point can accordingly correspond to a brighter pixel. Alternatively, the thermal image can be presented in pseudocolors, with different colors assigned to different intensity values. On the other hand, image points (pixels) that correspond to points of the surface with the same surface temperature have the same intensity value.

Then, based on the thermal image, an intensity distribution of the thermal radiation is ascertained relative to the respective number of pixels with the same intensity value. In other words, for each intensity value of the thermal image, the number of pixels with this intensity is determined. Thereafter, an intensity mean or, alternatively, an intensity median is ascertained from the intensity distribution based on the pixel count.

In addition, an intensity interval based on the intensity distribution is ascertained on the basis of a specifiable measure for a scattering of the intensity distribution. The specifiable measure for the scattering of the intensity distribution is based on the intensity mean/median. Preferably, a standard deviation or a quantile, in particular a quartile, of the intensity mean/median of the intensity distribution is ascertained as a measure for the scattering of the intensity distribution, and the intensity interval is defined on the basis of the standard deviation or the quantile. For example, the intensity interval corresponds to n times the standard deviation or quantile, in particular quartile (n is a decimal number, in particular a whole number greater than zero), for example, one or multiple times (e.g., two or three times) the standard deviation or the quantile, in particular quartile.

Then, a characteristic number is ascertained by addition of products, with, in each case, the products resulting from the number of pixels with the same intensity value multiplied by this intensity value. It is essential here that the products are added for only those intensity values that are greater than the intensity mean or intensity median increased by the intensity interval.

Then, the characteristic number thus ascertained or, alternatively, a calculation value based thereon is compared to a specifiable reference characteristic number, with a first evaluation result assigned to the layer system if the characteristic number is greater than or equal to the reference characteristic number, or a second evaluation result different from the first evaluation result assigned if the characteristic number is smaller than the reference characteristic number. The first evaluation result can, for example, be the statement "Layer system does not meet the required quality"; the second evaluation result can, for example, be the statement "Layer system meets the required quality".

As experiments of the applicant have demonstrated, using the method according to the invention, photovoltaic layer systems such as solar cells and solar modules can be subjected, in a simple manner, to an automated quantitative analysis and evaluation of their quality. The method enables layer systems with undesirably high internal power losses due to defects to be reliably detected with certainty such that compliance with quality requirements can be ensured.

As was already stated, in the method according to the invention, the current effecting a power loss can be generated by applying a voltage in the reverse-and/or forward-biased direction of the pn junction. If a voltage is applied in the reverse-biased direction, the electrical power loss develops substantially through the ohmic resistance of the semiconductor layer, with structuring lines that are formed in a solar module for an electrical series connection of the solar cells heating especially strongly. On the other hand, with a voltage applied in the forward-biased direction, predominantly the power losses in the cell region are detectable. Advantageously, in the method according to the invention, voltages with different polarity and/or different voltage values are applied, in particular in order to thus make different types of defects in the layer system distinguishable.

In another advantageous embodiment of the method according to the invention, the characteristic number ascertained is normalized, for example, by dividing it by a total characteristic number. The total characteristic number is calculated by adding products, resulting from the respective number of pixels with the same intensity value being multiplied by the intensity value, for all intensity values of the intensity distribution. In this case, it can also be advantageous if a quotient between the characteristic number and the total characteristic number is ascertained as a calculation value based on the characteristic number for comparison with the reference characteristic number. Alternatively, it can he advantageous to ascertain a difference between the characteristic number and the total characteristic number as a calculation value based on the characteristic number for comparison with the reference characteristic number.

In another advantageous embodiment of the method according to the invention, for a plurality of sections of the surface of the layer system different from one another, a separate characteristic number is ascertained in each case. The characteristic numbers ascertained for the various surface sections of the layer system enable a section-wise evaluation of the quality of the photovoltaic layer system, by means of which, in particular for the case that a high number of defects occur in specific sections, measures for improving the quality of the layer system can already be taken during production, targeted by the information about the spatial position. With this embodiment of the layer system, it can, in particular, be advantageous if the sections contain, in each case, at least one structuring line for the structuring of the layer system, since defects frequently occur in the region of the structuring lines.

Advantageously, the sections can also be formed in such a manner that they separate into regions that contain only the structuring lines and into regions that contain only pure cell portions.

The invention further relates to the use of a method as described above for the evaluating analysis of solar modules, in particular thin-film solar modules whose semiconductor layer is made of a chalcopyrite compound, in particular $Cu(In,Ga)(S,Se)_2$.

Figure 2B:
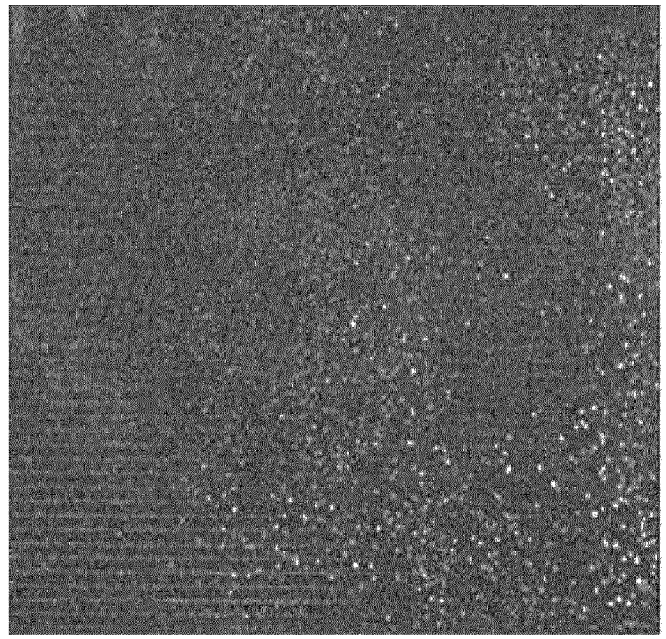
FIGS. 2A-2B shows thermal images of a solar module with a low defect count (FIG. 2A) and a high defect count (FIG. 2B)
Figure 2A:
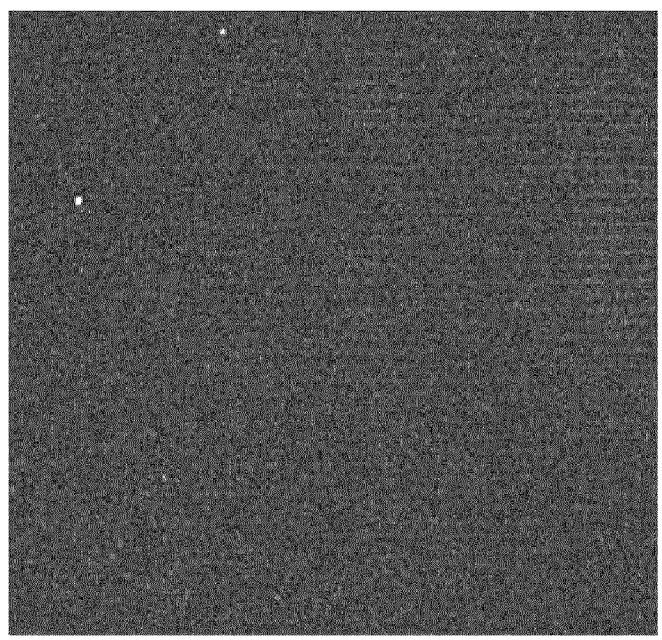
Figure 3:
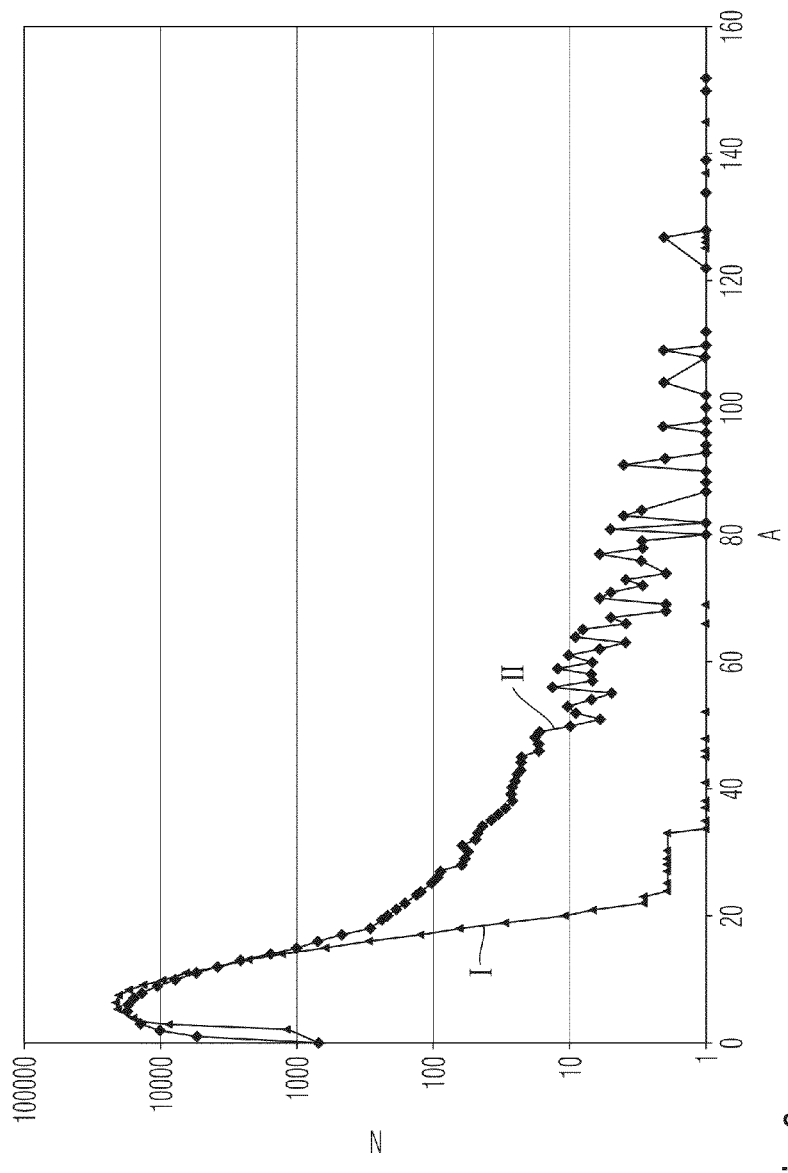
FIG. 3 shows a diagram to illustrate the intensity distributions of the thermal images of FIGS. 2A-2B.

The invention is now explained in detail using an exemplary embodiment and referring to the accompanying figures. They depict in simplified representation that is not to scale:

FIG. 1 a schematic representation of an exemplary setup for performance of the method according to the invention;

FIG. 2A-2B thermal images of a solar module with a low defect count (FIG. 2A) and a high defect count (FIG. 2B);

FIG. 3 a diagram to illustrate the intensity distributions of the thermal images of FIGS. 2A-2B.

FIG. 1 illustrates schematically an exemplary setup 1 for performance of the method according to the invention. Accordingly, the setup 1 includes a thin-film solar module 5 to be analyzed, which customarily has a plurality of solar cells serially connected in an integrated form for photovoltaic energy generation, which is not depicted in detail in FIG. 1.

As discernible from the enlarged representation of the thin-film solar module 5 of FIG. 1, each solar cell of thin-film solar module 1 can, for example, comprise the following layer system: On an insulating first substrate 11, made, for example, from glass with a relatively low light permeability, a back electrode layer 12, made, for example, from an opaque metal such as molybdenum (Mo), is disposed. A photovoltaically active absorber layer 13 made of a doped semiconductor is deposited on the back electrode layer 12. The absorber layer 13 is made, for example, of a p-conducting chalcopyrite semiconductor, in particular a compound of the group $Cu(In,Ga)(S,Se)_2$, for example, sodium (Na)-doped copper indium diselenide ($CInSe_2$). A buffer layer 14, made in this case, for example, of a single layer of cadmium sulfide (CdS) and a single layer of intrinsic zinc oxide (i-ZnO), is deposited on the absorber layer 13. A transparent front electrode layer 15, made, for example, of a doped metal oxide, for example, n-conducting aluminum (Al)-doped zinc oxide (ZnO), is applied on the buffer layer 14, for example, by vapor deposition. This forms a heterojunction, i.e., a sequence of layers of a different material type and opposing conductor type. For protection against environmental influences, an adhesive layer 16, made, for example, of polyvinyl butyral (PVB) and/or ethylene vinyl acetate (EVA), is applied on the front electrode layer 15. In addition, a second substrate 17 transparent to sunlight, which is made, for example, of low-iron extra white glass, is provided. The second substrate 17 is connected to the first substrate 11 by the adhesive layer 16 and serves to seal the layer system.

The thin-film solar module 1 can be produced easily and cost-effectively in industrial series production, with the various layers deposited on the first substrate 11 and structured to produce the serially connected solar cells using a suitable structuring technology such as laser writing and mechanical machining, for example, by stripping or scribing. Typically, such structuring comprises, for each solar cell, three structuring steps to produce three structuring lines, which are not shown in the enlarged representation of the thin-film solar module of FIG. 1.

As seen in FIG. 1, the thin-film solar module 5 is supported by its bottom side on a flat carrier 4 such that a light-entry-side top face or surface 10 of the thin-film solar module 5 is exposed. The thin-film solar module 1 is connected via first electrical lines 7 to a controllable voltage source 6 on two external connectors 9 disposed opposite each other, which are connected to the front or back electrode layers 12, 15 of the solar cells. An infrared camera 2, with which the thermal radiation of the surface 10 can be captured, spatially resolved, in a thermal image, is brought into position above the light-entry-side surface 10 of the thin-film solar module. As a rule, the thermal radiation corresponds to a heat distribution of the surface 10 of the thin-film solar module 1. Imaging optical elements of the setup 1 are not shown. Both the infrared camera 2 and the voltage source 6 are connected for data transmission via second electrical lines 8 to a processor-based control device 3.

Controlled by the control device 3, for a quantitative analysis of the thin-film solar module 5, first, an electric voltage is applied to the two external connectors 9 of the thin-film solar module 5 via the voltage source 6. This generates an electric current in the thin-film solar module 5, by means of which electrical power losses are induced, in particular in the region of defects of the thin-film solar module 5, which are detectable as local temperature elevations at the sites of the defects on the surface 10 of the thin-film solar module 5. The voltage applied is subject to a specific modulation, which is not discussed in detail here. Simultaneously or in a suitable temporal relation with the generation of current, a spatially resolved thermal image of the thermal radiation of the surface 10 of the thin-film solar module 5 is generated by the infrared camera 2.

By way of example, FIG. 2A and 2B depict two different thermal images for the case of a thin-film solar module 5 with a smaller defect count (FIG. 2A) and with a larger defect count (FIG. 2B). In the thermal images, the defects are detectable, in each case, as bright spots compared to the colder surroundings. The pixels corresponding to the defects thus have a higher intensity value that the pixels that correspond to the cooler defect surroundings. In both figures, fine parallel lines, which correspond to the structuring lines for the serial connection of the solar cells, are also detectable.

Then, an intensity distribution (histogram) of the thermal radiation relative to the respective number of pixels is ascertained from the thermal images. Such an intensity distribution is depicted in FIG. 3 as a diagram for the two thermal images of FIG. 2A and 2B. In the diagram, the amplitude or intensity is indicated in relative units as abscissa A; and the number N of pixels is indicated as the ordinate. Curve I corresponds to FIG. 2A; curve II corresponds to FIG. 2B. Clearly, curve II—corresponding to the larger defect count—has, in a middle amplitude region of the diagram, very many more pixels than curve I.

Then, an amplitude or intensity mean and the standard deviation are ascertained from the intensity distribution using conventional statistical methods. In the further evaluation, a characteristic number K is ascertained, by adding products, resulting, in each case, from the number of pixels with the same intensity value multiplied by this intensity value. The addition is performed here, for example, only for those intensity values that are greater than the intensity mean increased by the standard deviation.

As the result, a value $K_I$=157277 is obtained for curve I and a value $K_{II}$=273340 is obtained for curve II. Corresponding to the larger defect count, $K_{II}$ is significantly greater than $K_I$.

On the basis of this characteristic number K, an automated evaluation of the quality of the thin-film solar module 5 can now occur, with the characteristic number K compared to a definable reference characteristic number, wherein the thin-film solar module 5 is assigned a first evaluation result if the characteristic number K is greater than or equal to the reference characteristic number, or is assigned a second evaluation result different from the first evaluation result if the characteristic number K is less than the reference characteristic number.

The reference characteristic number depends on the specific quality requirements for the thin-film solar module 5. In the present exemplary embodiment, assume the reference characteristic number is, by way of example, 200000. Thus, for example, the evaluation result "Layer system meets the required quality" is assigned to the thin-film solar module 5 with a thermal image of FIG. 2A, which has a characteristic number $K_I$=157277; whereas, for example, the evaluation result "Layer system does not meet the required quality" is assigned to the thin-film solar module 5 with the thermal image of FIG. 2B, which has a characteristic number $K_{II}$=273340 and must accordingly be discarded.

The present invention makes available an automated method for the quantitative analysis of solar cells and solar modules that enables simple and reliable evaluation of their quality.

LIST OF REFERENCE SIGNS

1 Setup
2 Infrared camera
3 Control device
4 Carrier
5 Thin-film solar module
6 Voltage source
7 First electrical line
8 Second electrical line
9 Connector
10 Surface
11 First substrate
12 Back electrode layer
13 Absorber layer
14 Buffer layer
15 Front electrode layer
16 Adhesive layer
17 Second substrate

The invention claimed is:

1. A method for an evaluative analysis of a photovoltaic layer system, comprising the following steps:
generating an electric current in a layer system;
generating a spatially resolved image of a thermal radiation of a surface of the layer system, wherein the spatially resolved image has a multiplicity of pixels, each pixel of which is assigned an intensity value corresponding to a surface temperature of a point on the surface related to said pixel;
ascertaining an intensity distribution of the thermal radiation relative to a respective number of pixels with a same intensity value;
ascertaining an intensity mean/median from the intensity distribution;
ascertaining an intensity interval on a basis of a specifiable measure for a scattering of the intensity distribution;
ascertaining a characteristic number by addition of products, resulting in each case from the respective number of pixels with the same intensity value multiplied by the intensity value, for all intensity values above the intensity mean/median increased by the intensity interval; and
comparing the characteristic number or a calculation value based thereon with a specifiable reference characteristic number, wherein the layer system is assigned a first evaluation result if the characteristic number is greater than or equal to the specifiable reference characteristic number, or is assigned a second evaluation result if the characteristic number is less than the specifiable reference characteristic number.

2. The method according to claim 1, wherein the layer system comprises at least one semiconductor layer forming a pn junction.

3. The method according to claim 2, wherein an electric current is generated in the layer system by applying an electric voltage in a reverse- and/or forward-biased direction of the pn junction.

4. The method according to claim 3, wherein electric voltages with different polarity and/or different magnitude are applied.

5. The method according to claim 1, wherein the electric current in the layer system is generated by irradiating the layer system with light.

6. The method according to claim 1, wherein the intensity interval is calculated on a basis of a standard deviation or a quantile of the mean/median of the intensity distribution.

7. The method according to claim 6, wherein the intensity interval is calculated on the basis of the quantile of the mean/median of the intensity distribution.

8. The method according to claim 1, wherein the characteristic number is normalized, by dividing the characteristic number by a total characteristic number that results from the addition of products resulting in each case from the number of pixels with the same intensity value multiplied by the intensity value for all intensities of the intensity distribution.

9. The method according to claim 8, wherein a quotient between the characteristic number and the total characteristic number is ascertained as a calculation value for a comparison with the specifiable reference characteristic number.

10. The method according to claim 8, wherein a difference between the characteristic number and the total characteristic number is ascertained as a calculation value for a comparison with the specifiable reference characteristic number.

11. The method according to claim 1 wherein the characteristic number is ascertained in each case for a plurality of sections of the surface of the layer system different from one another.

12. The method according to claim 11, wherein the plurality of sections contain, in each case, at least one structuring line for a structuring of the layer system.

13. The method according to claim 11, wherein separate sections of the plurality of sections are formed, wherein separations occur according to regions with at least one structuring line and regions with pure cell portions.

14. A method comprising:
using the method according to claim 1 for evaluating analysis of solar modules.

15. The method according to claim 14, wherein the solar modules are thin-film solar modules, whose semiconductor layer is made of a chalcopyrite compound.

16. The method according to claim 15, wherein the chalcopyrite compound is $Cu(In,Ga)(S,Se)_2$.

* * * * *